(12) United States Patent
Mongale et al.

(10) Patent No.: US 8,808,981 B2
(45) Date of Patent: Aug. 19, 2014

(54) POINT-OF CARE, MEDICAL CONDITION SCREENING KIT

(75) Inventors: Sean Mongale, Jacksonville, FL (US); Shishira Nagesh, Bangalore (IN); Ezra Taylor, Pike Road, AL (US); Mary O'Grady, Anchorage, AK (US); Thembi Mdluli, West Lafayette, IN (US); Peter Truskey, Durham, NC (US); Sherri Hall, Cary, IL (US); James Waring, III, Baltimore, MD (US); Britni Crocker, Long Valley, NJ (US); Harshard Sanghvi, Reisterstown, MD (US); Elaine Yang, Newark, DE (US); Soumyadipta Acharya, Baltimore, MD (US); Maxim Budyansky, Hartford, CT (US); Matthew Means, Baltimore, MD (US)

(73) Assignee: Jhpiego Corporation, Baltimore, MD (US)

( * ) Notice: Subject to any disclaimer, the term of this patent is extended or adjusted under 35 U.S.C. 154(b) by 0 days.

(21) Appl. No.: 14/115,691

(22) PCT Filed: May 7, 2012

(86) PCT No.: PCT/US2012/036776
§ 371 (c)(1),
(2), (4) Date: Nov. 5, 2013

(87) PCT Pub. No.: WO2012/154672
PCT Pub. Date: Nov. 15, 2012

(65) Prior Publication Data
US 2014/0093896 A1    Apr. 3, 2014

Related U.S. Application Data

(60) Provisional application No. 61/483,482, filed on May 6, 2011, provisional application No. 61/563,274, filed on Nov. 23, 2011, provisional application No. 61/563,281, filed on Nov. 23, 2011, provisional application No. 61/563,285, filed on Nov. 23, 2011.

(51) Int. Cl.
*C12Q 1/00*    (2006.01)

(52) U.S. Cl.
USPC ............. 435/4; 435/975; 422/402; 422/420; 422/430

(58) Field of Classification Search
USPC ................ 435/4, 975; 422/402, 420, 430
IPC .................. C12Q 31/22; G01N 31/22,33/52
See application file for complete search history.

(56) References Cited

U.S. PATENT DOCUMENTS

| 2005/0214161 A1* | 9/2005 | Gupta | ............................ 422/56 |
| 2013/0089858 A1* | 4/2013 | Wong et al. | ................... 435/6.1 |

FOREIGN PATENT DOCUMENTS

WO    WO 2011/009893    *    1/2011

OTHER PUBLICATIONS

Voswinckel P. A Marvel of Colors and Ingredients. The Story of Urine Test Strips. Kidney Int 47(5 Suppl)S3-7, Nov. 1994.*

* cited by examiner

*Primary Examiner* — Ralph Gitomer
(74) *Attorney, Agent, or Firm* — Larry J. Guffey

(57) ABSTRACT

A point-of-care, screening kit for use by a heath care worker to create custom test strips for screening the bodily fluids of an individual for various, medical conditions includes: (a) a plurality of reagents (12), (b) a substrate (18) configured to: i) receive one of the reagents and react with it so as to cause it to acquire a first characteristic color, and, ii) upon the addition of the individual's bodily fluid to the substrate, acquire, as a result of the formulation of each of the reagents, a second, dichotomous characteristic color when the individual has a specific one of the various, medical conditions. This kit also includes: (c) a plurality of containers (10) having indicia (26) that are reflective of the reagent within the container and which of the various medical conditions is being screened for with the use of the container and the characteristic first and second colors which are indicative of the individual having a screened for medical condition, and (d) one of the reagents being a protein reagent that includes appropriate quantities of: water, isopropyl alcohol, citric acid monohydrate, sodium citrate iribasic monohydrate, tetrabromophenol blue and tartrazine.

24 Claims, 7 Drawing Sheets

| Chemical | Sigma-Aldrich Product Number (CAS Number) | Purpose | Chemical Formula |
|---|---|---|---|
| Water | -- (7732-18-5) | Solvent | $H_2O$ |
| Isopropyl Alcohol | I9030 (67-63-0) | Solvent (dissolve Tetrabromophenol Blue), Biocide | $H_3C\!-\!CH(OH)\!-\!CH_3$ |
| Citric Acid Monohydrate | C7129 (5949-29-1) | Citric Acid Buffer | (structure) $\cdot H_2O$ |
| Sodium Citrate tribasic dihydrate | S4641 (6132-04-3) | Citric Acid Buffer | (structure) |
| Tetrabromophenol Blue | 199311 (4430-25-5) | Protein (albumin) indicator | (structure) |

*Polyvinylpyrrolidone K90 (10%) components:

| Chemical | Sigma-Aldrich Product Number (CAS Number) | Purpose | Chemical Formula |
|---|---|---|---|
| Water | -- (7732-18-5) | Solvent | $H_2O$ |
| Polyvinylpyrrolidone K90 | 81440 (9003-39-8) | Thickener |  |

**Citrate Buffer components:

| Chemical | Sigma-Aldrich Product Number (CAS Number) | Purpose | Chemical Formula |
|---|---|---|---|
| Water | -- (7732-18-5) | Solvent | $H_2O$ |
| Citric Acid Monohydrate | C7129 (5949-29-1) | Citric Acid Buffer | 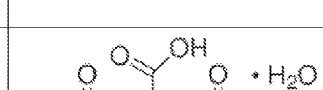 |
| Sodium Citrate tribasic dihydrate | S4641 (6132-04-3) | Citric Acid Buffer | 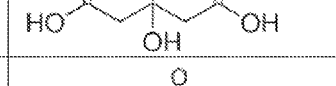 |

FIG. 6
| Chemical | Sigma-Aldrich Product Number (CAS Number) | Purpose | Chemical Formula |
|---|---|---|---|
| Methanol | 322415 (67-56-1) | Solvent | $CH_3OH$ |
| Sulfanilamide | S9251 (63-74-1) | Form Diazonium Salt in presence of nitrite ions | 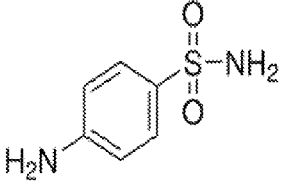 |
| 1-naphthylamine | 70731 (134-32-7) | Coupling agent (reacts with Diazonium Salt to create red dye) | 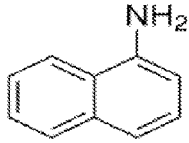 |
| DL - Tartaric Acid | T400 (133-37-9) | Acidic environment for reaction | 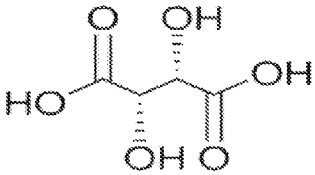 |

FIG. 7

| Chemical | Sigma-Aldrich Product Number (CAS Number) | Purpose | Chemical Formula |
|---|---|---|---|
| Water | --- (7732-18-5) | Solvent | $H_2O$ |
| Potassium Ferricyanide | 702587 (13746-66-2) | Ketone Indicator | $3K^+$ $[Fe(CN)_6]^{3-}$ |
| Tris(hydroxymethyl) aminomethane | 252859 (77-86-1) | Basic Buffer | $(HOCH_2)_3CNH_2$ |
| Magnesium Sulfate heptahydrate | M1880 (10034-99-8) | Nitroprusside stabilizer | $MgSO_4 \cdot 7H_2O$ |

POINT-OF CARE, MEDICAL CONDITION SCREENING KIT

This application is a National Stage application filed under Rule 371 based on PCT/US12/36776 filed May 7, 2012

CROSS-REFERENCE TO RELATED APPLICATION

This application claims the benefit of the following Provisional Patent Applications No. 61/483,482—filed May 6, 2011, No. 61/563,274 filed Nov. 23, 2011, No. 61/563,281 filed Nov. 23, 2011, and No. 61/563,285 filed Nov. 23, 2011; all filed by the present inventors. The teachings of these applications are incorporated herein by reference to the extent that they do not conflict with the teaching herein.

BACKGROUND OF THE INVENTION

1. Field of the Invention

The present invention relates generally to analytical testing devices and methods. More particularly, the invention relates to a point-of-care, screening kit and methods for use by heath care workers, with minimal training, to screen the bodily fluids of individuals for various medical conditions that can, if untreated, later result in severe, medical complications for the individual.

2. Description of the Related Art

Point-of-care testing of bodily fluid specimens, such as urine, saliva, mucus, and sputum, has become well known in today's society as part of a physician's process of diagnosing the medical condition of a patient. Such tests frequently involve the use of various types of test strips (or dipsticks) that have been especially formulated so that one or more portions of them change their color when exposed to an individual's bodily fluids; thereby giving some indication of the medical condition of the individual who supplied the bodily fluid.

These indications arise because the various portions of such strips having been treated with reagents which chemically react with an individual's bodily fluids so as to yield color changes that are indicative of various tested-for, medical conditions. Although such test strips are widely used in many parts of the world, their use in developing countries is often hindered because the prices of these test strips are frequently too expensive and therefore cannot be afforded by the citizens of developing countries or the institutions that provide their medical care.

The consequences of not testing for certain medical conditions, which such test strips could identify, can be devastating. Each year, more than six million pregnant women and newborns die due to complications from pregnancy and childbirth a staggering 99% of these maternal deaths occur in developing countries and many could have been prevented if pre-natal screening had been used to help identify and then treat the underlying medical conditions that yielded these complications.

For example, pre-eclampsia and eclampsia, which alone cause 76,000 maternal and 500,000 infant deaths per year, primarily in developing countries, can, if detected early using existing screening tests, generally be easily treated with steroids and magnesium sulfate. However, at approximately twenty US cents per test strip, currently available test strips for these conditions are too expensive for widespread use in many developing countries.

Additionally, some of the current combinations of reagents and test strips yield only small comparative color changes and therefore are often difficult to accurately interpret by health care workers who have not had extensive training. This situation has limited their use in many developing countries whose health care is workers often have minimal medical training.

Accordingly, there exists a need for low-cost, point-of-care tests for use by heath care workers in developing countries to screen the bodily fluids of individuals, especially pregnant women, for various, medical conditions that can, if untreated, later result in severe, medical complications for the individuals.

SUMMARY OF THE INVENTION

Recognizing the need for the development of improved point-of-care screening tests, especially for use in developing countries, the present invention is generally directed to overcoming the problems and disadvantages exhibited by existing, point-of-care screening tests.

In accordance with the present invention, a low-cost, point-of-care, screening kit for use by heath care workers with minimal training to screen the bodily fluids of individuals for various, medical conditions that can, if untreated, later result in severe, medical complications for the individuals includes: (a) a plurality of reagents, (b) a substrate having an outer surface that is configured to: i) receive one of the reagents and react with it so as to cause the substrate's outer surface to acquire a first characteristic color, and, ii) upon the addition of a specified quantity of an individual's bodily fluid to a portion of the substrate containing the reagent, acquire, is as a result of the formulation of each of the reagents, a second, dichotomous characteristic color, and wherein the substrate outer surface's acquisition of this second characteristic color is indicative of the individual having a specific one of the various, tested-for medical conditions.

This screening kit also includes: (c) a plurality of containers, each of which has an outer surface that includes an orifice and is configured to receive, store and dispense a prescribed quantity of one the plurality of reagents, (d) a plurality of container closing means, each of which is configured to cover the orifice of one the containers, and wherein, to aid the health care workers in properly using this screening kit, each of the containers' outer surfaces and their closing means are configured with indicia that are reflective of the reagent within the container and which of the various medical conditions is being screened-for with the use of the container and the characteristic first and second colors which are indicative of the individual having a screened for medical condition.

In a preferred embodiment this point-of-care screening kit, it also includes a protein reagent that is configured to test for the presence of protein when the bodily fluid of the individual is urine, and wherein this protein reagent includes appropriate quantities of the following components: water, isopropyl alcohol, citric acid monohydrate, sodium citrate tribasic monohydrate, tetrabromophenol blue and tartrazine. Appropriate quantities of these components lie within the range of: water—5-10 mL, isopropyl alcohol—O-5 mL, citric acid monohydrate—1-1.5 g, sodium citrate tribasic monohydrate—0.22-0.65 g, tetrabromophenol blue—5-15 mg, and tartrazine—0-15 mg.

Thus, there has been summarized above (rather broadly and understanding that there are other preferred embodiments which have not been summarized above) the present invention in order that the detailed description that follows may be better understood and appreciated.

BRIEF DESCRIPTION OF THE DRAWINGS

FIG. 4 is a table that provides a more detailed chemical description of the components which make up a protein reagent that is suitable for use with the present invention.

FIG. 5(b) are tables that provide a more detailed chemical description of the polyvinylpyrrolidone K90 (10%) and citrate buffer components of the glucose reagent disclosed in FIG. 5(a).

FIG. 6 is a table that provides a more detailed chemical description of the components which make up a nitrite reagent that is suitable for use with the present invention.

FIG. 7 is a table that provides a more detailed chemical description of the components which make up a ketone reagent that is suitable for use with the present invention.

DESCRIPTION OF THE PREFERRED EMBODIMENT

Figure 1:
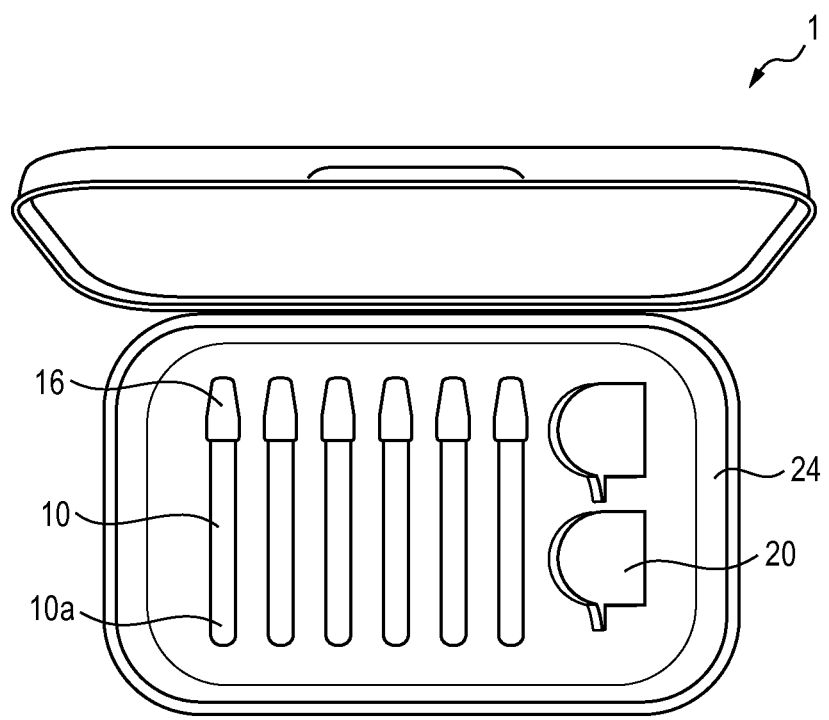
FIG. 1 is a top view of an exemplary embodiment of the present invention in the form of a low-cost screening kit for use by heath care workers to screen the bodily fluids of a pregnant woman for various, medical conditions that can, if untreated, later result in severe, medical complications for both the woman and her fetus.
Figure 2A:
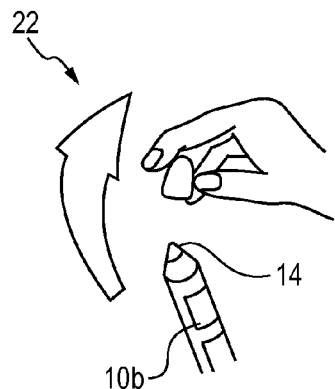
FIG. 2 illustrates exemplary pictorial instructions that are provided to aid a health care worker in administering the screening test of the present invention.
Figure 2B:
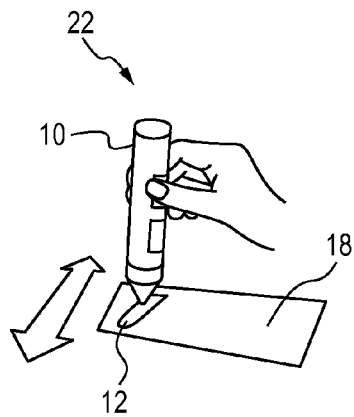
Figure 2C:
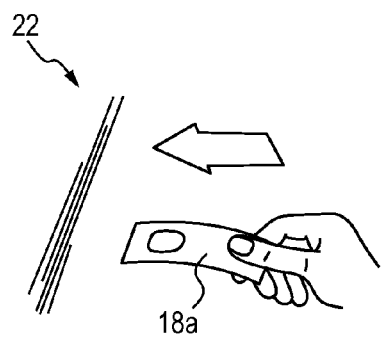
Figure 2D:
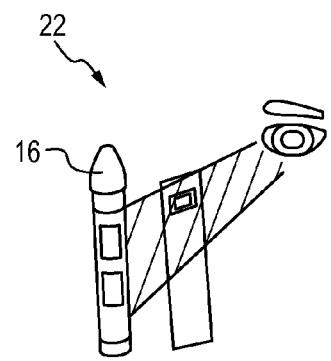

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention pertains to a novel and extremely affordable method for screening an individual's bodily fluids to make a qualitative positive or negative test result) or quantitative assessment of the individual for various medical conditions, such as: (a) pre-eclampsia and eclampsia, (b) diabetes, (c) malnutrition, (d) urinary tract infections, (e) pH of the bodily fluid, and (f) blood is in bodily fluid, etc. The current option for screening for most of these conditions is a urine dipstick which costs an average of twenty US cents per strip or test and therefore is not suitable for widespread use in cost-conscious and resource-constrained settings such as in developing countries.

Disclosed herein is a screening kit which can be used to create various point-of-care tests; thereby removing several manufacturing and packaging steps involved in the making conventional dipsticks or test strips, and thus reducing the overall costs of such screening tests. The present invention discloses a kit containing blank test strips and multiple reagent delivery devices which are required to make custom diagnostic test strips at the point-of-care. This invention alters the way a test strip can be made—it provides a health care worker with the necessary components to create low-cost, custom test strips that can be used at a patient's point of care to effectively screen a patent for a variety of medical conditions.

For example, a health care worker may want to only give a patient a protein test and a glucose test. With conventional urine test strips, the health care worker would be forced to use a multi-test, urine dipstick, which typically is configured to screens for up to eight other analytes urine. Using such conventional urine dipsticks is a waste of both materials and money. With the present invention, a health can worker can now create a custom test strip using a protein reagent container or delivery device and a glucose reagent delivery device.

The present invention can bring the cost of screening for various medical conditions down to 0.5 US cents per custom test strip down from the conventional dipstick cost of 20 US cents per test. FIG. 1 shows a top view of the preferred embodiment of the present invention 1. This preferred embodiment consists of a series of pens, containers, delivery devices or platforms 10, each of which is filled with an especially selected reagent 12, and has a reagent-dispensing tip 14 and a cap or closing means 16 that covers the container's reagent-dispensing tip when it is not in use.

It also includes a substrate or filter paper 18 that is contained in a dispenser 20 and will usually include pictorial instructions 22, see FIGS. 2(a)-2(d), to help guide a health care worker to create a custom test strip and to help assure the proper use of the present invention's screening tests. All of these items are housed in a is portable enclosure 24 and together comprise the present invention's screening kit.

Each of the containers 10 has an outer surface 10a that includes an orifice 10b and is configured to receive and store one of the selected reagents. This orifice 10b is later plugged by a reagent-dispensing tip 14. The container and its cap 16 are color coded so as to contain the characteristic colors that are used in testing an individual for a specific medical condition. For example, the container's outer surface 10a may be colored or contain at least a portion that is of the same color that the substrate will assume once it has been treated with the reagent contained in the container.

A second color is either also on the container's outer surface 10a or is on the container's cap 16 and this color indicates the color which the substrate will take on once it has been subjected to an individual's bodily fluid and given time to chemically react with the reagent which has been placed on the substrate and if the test is positive for the tested-for medical condition of the individual. These color markings or markings which communicate the same information are considered for the purpose of this application to be describable as in the broadest terms as indicia 26. Written or text messages, also considered as indicia, may also be included on the container's outer surface which are reflective of the reagent within the container and which of the various medical conditions is being screened for with the use of the container.

The reagents 12 are so designed to provide a color change when a specific pathological condition exists in the bodily fluid sample deposited on the substrate. For example, the color of the substrate or strip when treated with the novel protein reagent of the present invention and exposed to a pregnant woman's urine changes from yellow to blue in the presence of protein in the urine and is indicative of a positive test for pre-eclampsia in the pregnant woman. Different color-coded containers or pens have different reagents and are used to test an individual for different medical conditions.

While the containers or platforms 10 of the present invention have been described above and shown in FIG. 1 as pens, it should be noted that under certain conditions and with certain reagents these containers may take other forms, such as asthma inhalers or spray dispensers. Additionally, in selecting a proper container, is one has to ensure that its materials of construction are such that they will not react with the reagents being stored in them while protecting the reagent from degradation during the period it is stored in the container.

Figure 3:
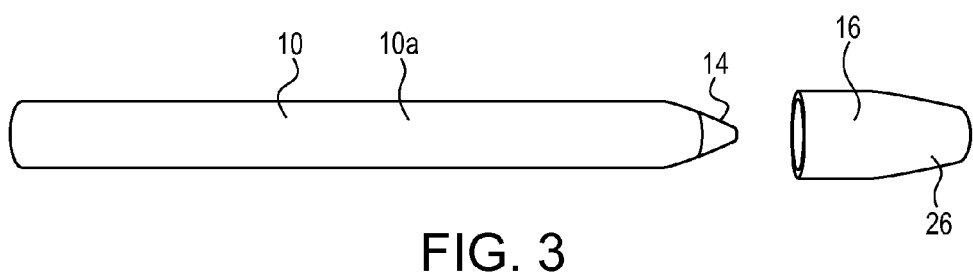
FIG. 3 shows a close-up view of a container with its reagent-dispensing tip and cap in an exemplary embodiment of the present invention.

Each of this series of containers has an especially designed reagent-dispensing tip 14 that is configured to dispense a prescribed quantity of one of the plurality of reagents. See FIG. 3. The proper dispensing of reagent may also be aided by placing indicia on the substrate. For example, various diameter circles or various size ellipses can be added around the center points of the substrate portions where the reagent is to be dispensed to indicate when 20 μL or a set volume of reagent has wicked into the substrate. In a preferred embodiment, the tip 14 has a valve or means (e.g., a specialized shutter-ball mechanism which must be depressed and the container squeezed in order to allow fluid to be dispensed—this mechanism decreases the chance of accidental leakage and allows free flow of all the molecules within the reagent onto the substrate) that is configured to dispense reagent only upon a certain level of pressure applied to a substrate's outer surface and a gentle squeezing of the container.

Since the reagent remains in liquid state within the container, it accommodates reagents with large molecules and enables them to be effectively and precisely delivered onto a portion of a substrate. The container's light-opaque nature protects the reagent from light degradation.

As mentioned above, the substrate 18 of the present invention has an outer surface 18a that is configured to: a) receive one of the reagents and react with it so as to cause the substrate outer surface's to acquire a first characteristic color, and, b) upon the addition of a specified quantity of an individual's bodily fluid to a portion of the substrate that has been treated or coated with a specific concentration of the reagent, acquire a second characteristic color, which is dichotomous with the first characteristic color, if the screening result is positive for the medical condition for which the individual is being tested/screened, and wherein the substrate outer surface's acquisition of this second dichotomous characteristic color is therefore indicative of a positive test and the individual having a specific medical condition. To assist in assuring the proper conduct of such a screening test, these pairs of characteristic colors are shown on the outer surfaces of the containers and their caps.

Many types of substrate 18 can be used with the present invention, including various filter papers (e.g., coffee filter, laboratory filter papers—e.g., a Whatman grade 1 filter paper), cotton materials, nitrocellulose materials, regular papers, newspaper material. When the bodily fluid to be used in the screening test is blood, the substrate may also be treated with blood separating chemicals. In addition to being configured into a strip or roll-like material that can be wound on the dispenser 20 shown in FIG. 1, the substrate can also be configured as booklet of paper or other substances which perforated strips for separating individual test strips.

The enclosure 24 of the present invention is preferably configured such that it is water resistant and light or photo opaque so as to protect and safely transport the pens and papers which the enclosure stores.

If the containers 10 of the present invention were to be formed as pens, as shown in FIG. 1, they could conceivably be mass produced in the same assembly line fashion as that used for conventional high-liter-type-marker production with certain modifications. These include: (a) replacing the ink or high-liting liquid with different reagents to be filled into the pens, (b) modifying the outer surface of the pen and its cap to indicate the color changes to be used in testing for the medical condition associated with the reagent contained in the pen so as to aid the health care worker in properly administering and interpreting the results of the screening test. For example, the pen that's used to test for proteinaria has a yellow container and a blue cap to show that the color changes from yellow to blue when a positive test result is achieved. Such a yellow container can also have a blue stripe that helps identify the respective container body onto which the blue cap is to be fitted.

The method of using the present invention involves a health care worker or provider first tearing a strip of the substrate or filter paper from the dispenser. The provider then uncaps the container or pen—see FIG. 2(*a*), applies or marks the reagent onto the strip—see FIG. 2(*b*), and waits for this marked portion strip to assume its first characteristic color (as possibly shown on the container). This marked strip is then provided it to the individual who is to be screened for the specific medical condition that corresponds to the reagent added to the substrate. The individual deposits a bodily fluid onto the reagent-marked portion of the strip; alternatively, this deposition can occur by other means, including: (a) dipping the test strip in the bodily fluid or liquid sample, (b) adding the liquid sample drop-by-drop to the test strip, (c) direct urination upon the test strip by the individual being screened—see FIG. 2(*c*). The health care worker then visually examines the reagent wetted portion of the strip assumes the screening test's second characteristic color (as possibly shown on the container's cup) see FIG. 2(*d*), the individual is identified as positive for the screened-for, medical condition. If no color change is observed, the health care provider diagnoses the individual as negative for the screened-for medical condition. Pictorial instructions, see FIG. 2(*a*)-(*d*), are provided to aid the health care provider.

Many types of diagnostic and/or screening reagents 12 have been found suitable for use with the present invention. These include those that can be used to provide point-of-care screening of bodily fluids for the presence of: protein, glucose, nitrites, leukocytes, ketone bodies, bilirubin and urobilinogen, plus test the bodily fluid for its specific gravity and pH level.

A preferred embodiment of the protein reagent of the present invention tests for the presence of the protein albumin. Albumin is relatively abundant in the human body and is normally filtered by the kidneys (removing the protein from urine). The presence of albumin in the urine is one of the first signs that the kidneys may be malfunctioning or failing. In the case of pregnant women, proteinuria is one of the two diagnostic symptoms of pre-eclampsia and eclampsia—a condition of high blood pressure that arises during pregnancy and can have dire consequences if untreated.

An improved and more color-sensitive formulation for the protein reagent of the present invention has components whose appropriate quantities lie within the range of: water—5-10 mL, isopropyl alcohol—0-5 mL, citric acid monohydrate—1-1.5 g, sodium citrate tribasic monohydrate—0.22-0.65 g, tetrabromophenot blue—5-15 mg, and tartrazine—0-15 mg; with a preferred formulation being: water—6.5 mL, isopropyl alcohol—3.5 mL, citric acid monohydrate—1.3 g, sodium citrate tribasic monohydrate—0.65 g, tetrabromophenot blue—7.5 mg and tartrazine 10 mg. For best results, these components should be added in the order listed above and mixed thoroughly (at least 5-10 minutes); there are no special procedural steps (e.g., heating) required. See FIG. 4 for a more complete chemical description of these components.

Most protein reagents that are used on urine dipsticks (i.e., used for the detection of proteins in urine) consist of a color-changing protein indicator, such as tetrabromophenol blue (TBPB), and a buffer to protect the reagent from the urine pH.

The present invention details a new reagent that is extremely sensitive to the presence of proteins and consequently exhibits a significant increase in the degree of the color change on a dipstick or test strip.

Many currently manufactured urine test strips or dipsticks, for protein screening, exhibit a gradual color change, for example: light green for negative samples, uniform green for protein in urine concentrations of 0.30-1.0 g protein/L of urine (g/L) and which register on a dipstick as +1, or for concentrations of 1.0-3.0 g/L which register on a dipstick as +2, and finally turning a dark green or teal color for samples that register +3 at concentrations of 3.0-20.0 g/1- or +4 for concentrations >20.0 g/L.

Even when one tries to interpret these color changes with the use of a color chart that is provided with the dipstick, much variability can be found in the interpreted results. These test interpretation difficulties make it unrealistic for the typical urine dipstick that is used for protein screening to be used widely in settings where they will be utilized by untrained individuals or health care workers who have minimal medical training.

However, the dichotomous color change yielded by the protein reagent of the present invention not only decreases screening errors, but does so in a manner that does not require the use of an accompanying color chart. Thus, the present invention makes significantly lower-cost, point-of-care protein screening possible developing countries. A significant improvement or technical contribution of the present invention is the disclosure of various reagents that yield dichotomous color changes which are easy for even minimally trained health care workers to distinguish the screening test's results as being either positive or negative.

The improved protein reagent of the present invention exhibits a much greater and more sensitive range of color change, beginning with yellow for samples with negative protein and up to 0.20 g/L, to green for a protein concentration of around 0.40 g/L and then turning to its final color of blue for samples with protein concentrations greater than or equal to 0.74 g/L. The protein reagent of the present invention therefore undergoes a full dichotomous color change from yellow to blue within a protein concentration range of 0.3-0.4 g/L.

A preferred embodiment of the glucose reagent of the present invention tests for the glycosuria (glucose in the urine), which is an important screening test for pregnant women. Glycosuria is typically an indicator of high blood glucose levels. In developed countries glycosuria is an important screening test for Gestational Diabetes (GD), which is diabetes that develops during pregnancy for a woman without previous hyperglycemia.

In developing countries, screening for glycosuria during pregnancy is even more important because a larger percentage of these women are usually unaware of any pre-existing hyperglycemic conditions that they may have. When a pregnancy is complicated with high blood glucose, the perinatal outcomes are significantly worse. Hyperglycemia raises the risk of congenital malformation and perinatal mortality. It is also directly associated with fetal hyperglycemia and fetal cardio-respiratory distress. The effects of hyperglycemia also vary based the period of the pregnancy. Treatment during the first trimester reduces the risk of fetal anomalies and fetal demise. Treatment during the second and third trimesters reduces the risk of adverse perinatal and neonatal outcomes. Finally hyperglycemia can increase the risk of the pregnancy for the mother.

Figure 5A:
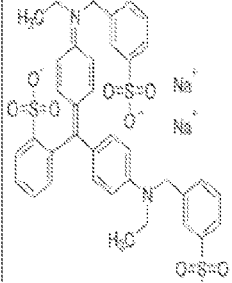
FIG. 5(a) is a table that provides a more detailed chemical description attic components which make up a glucose reagent that is suitable for use with the present invention.

A typical formulation for the glucose reagent of the present invention is glucose oxidase—0.26 g, horseradish peroxidase—2.4 mg, potassium iodide—0.5 g, erioglaucine—5.2 mg, polyvinylpyrrolidone K90 (10%)—2.5 (water—2.5 mL, polyvirtylpyrrolidone K90—0.25 g) citrate buffer (ph 5.5)—26.5 mL (water 26.5 mL, citric acid monohydrate—0.18 g, sodium citrate tribaseic dehydrate—0.53 g) and water—16.5 ml. See FIGS. 5(*a*)-5(*b*) for a more complete chemical description of these components.

A preferred embodiment of the nitrite reagent of the present invention tests for the presence of nitrites in urine as means of providing a screening for urinary tract infections (UTIs). This situation arises because nitrates ($NO_3^-$) are normally present in urine and some bacteria that infect the urinary tract can turn these nitrates into nitrites ($NO_2^-$). However, many bacteria and viruses that infect the urinary tract may not cause this conversion to take place, which is one reason that this test is often coupled with a test to detect leukocyte esterase to screen for UTIs.

A typical formulation for the nitrate reagent of the present invention is methanol—10 mL, sulfanilamide—0.01 g, N,N-Dimethyl-1-naphthylamine—100 µL and DL-tartaric acid—0.25 g. See FIG. 6 for a more complete chemical description of these components.

A preferred embodiment of the ketone reagent of the present invention tests for the presence of abnormally high levels of ketones in the body. These are formed when the body breaks down fats instead of glucose for energy. When this occurs, three ketone bodies are formed: Acetone: $(CH_3)_2CO$, Acetoacetic acid: $CH_3C(O)CH_2CO_2H$ and β-Hydroxybutyric acid: $C_4H_8O_3$. High levels of ketones in the body can be caused by starvation, digestive disorders, diabetes and several other conditions. This test is often combined with a glucosuria test to screen for diabetes or gestational diabetes in pregnant women. Two of the ketone bodies are acidic, and the accumulation of these chemicals can lead to a drop in blood pH, a condition called ketoacidosis. So ketones not only indicate the previously listed conditions but they themselves can be dangerous in elevated quantities.

A typical formulation for the ketone reagent of the present invention is water—10 mL, potassium fetricyanide—0.1 g, tris(hydroxymethyl)aminomethane—1.7 g and magnesium sulfate heptahydrate—0.5 g. See FIG. 7 for a more complete chemical description of these components.

Other reagents for use with dipsticks and test strips are well known in the art and are also suitable for use with the present screening kit. These will not be described further herein, but are considered to come within the scope of the present invention.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that are set forth in the claims to the invention.

The invention claimed is:

1. A point-of-care screening kit (1) for use by heath care workers to make custom test strips to screen the bodily fluids of an individual for various, medical conditions, said kit comprising:

a reagent (12), a substrate (18) having an outer surface (18*a*) that has a configuration adapted is configured to: a) receive said reagent (12) and react with said reagent so as to cause said substrate outer surface to acquire a first characteristic color that is indicative of one of said medical conditions for which said screening is being undertaken, and, b) upon the addition of a specified quantity of said bodily fluid of said individual to a portion of said substrate containing said reagent, acquire a second characteristic color that is indicative of said individual having said medical conditions for which said screening is being undertaken, a container (10) having an outer surface (10a) that includes an orifice (10b), said container having a configuration adapted configured to receive and store a prescribed quantity of said reagent (12), and a reagent-dispensing tip (14) that has a configuration adapted to dispense said reagent which is stored in said container.

2. The point-of-care screening kit as recited in claim 1, wherein:
said container outer surface (10a) has indicia (26) that is indicative of one of said characteristic colors which are involved with said screening for one of said medical conditions.

3. The point-of-care screening kit as recited in claim 1, further comprising:
a container closing means (16) which has a configuration adapted to cover said reagent-dispensing tip (14) of said container when said reagent-dispensing tip is not in use.

4. The point-of-care screening kit as recited in claim 2, further comprising:
a container closing means (16) which has a configuration adapted to cover said reagent-dispensing tip (14) of said container when said reagent-dispensing tip is not in use.

5. The point-of-care screening kit as recited in claim 3, wherein:
said container closing means (16) has indicia (26) that is indicative of one of said characteristic colors which are involved with said screening for one of said medical conditions.

6. The point-of-care screening kit as recited in claim 4, wherein:
said container closing means (16) has indicia (26) that is indicative reflective of one of said characteristic colors which are involved with said screening for one of said medical conditions.

7. The point-of-care screening kit as recited in claim 1, wherein:
said reagent (12) has a configuration adapted to yield a dichotomous color change on said substrate, and
said substrate is a filter paper having a configuration selected from the group consisting of a roll or pre-perforated strips, individual strips and individual sheets.

8. The point-of-care screening kit as recited in claim 7, wherein:
said reagent (12) is a protein reagent that has a configuration adapted is configured to test for the presence of protein when said bodily fluid of said individual is urine, and wherein said protein reagent includes appropriate quantities of the following components: water, isopropyl alcohol, citric acid monohydrate, sodium citrate tribasic dihydrate, tetrabromophenol blue and tartrazine.

9. The point-of-care screening kit as recited in claim 8, wherein:
said appropriate quantities of said protein reagent components are in the range of: water—5-10 mL, isopropyl alcohol—0-5 mL, citric acid monohydrate—1-1.5 g, sodium citrate tribasic dihydrate—0.22-0.65 g, tetrabromophenol blue—5-15 mg, and tartrazine—0-15 mg.

10. The point-of-care screening kit as recited in claim 1, wherein:
said reagent (12) is a plurality of reagents selected from the group consisting of reagents used to screen for: (a) protein, (b) glucose, (c) nitrites, (d) leukocytes, (e) ketone bodies, (f) bilirubin, and (g) urobilinogen,
said container (10) is a plurality of containers, each of which has a configuration adapted to receive and store one of said plurality of reagents,
said reagent-dispensing tip (14) is a plurality reagent-dispensing tips, each of which has a configuration adapted to dispense a uniform, prescribed quantity of said reagent that is stored in said container with which said reagent-dispensing tip is associated, and
wherein each of said container outer surfaces (10a) has indicia (26) that is indicative of one of said characteristic colors which are involved with said screening for one of said medical conditions.

11. The point-of-care screening kit as recited in claim 10, wherein:
each of said reagents (12) has a configuration adapted to yield a dichotomous color change on said substrate.

12. The point-of-care screening kit as recited in claim 1, wherein:
said reagent (12) is a plurality of reagents, each of which has a configuration adapted to yield a dichotomous color change on said substrate,
said container (10) is a plurality of containers, each of which has a configuration adapted to receive and store one of said plurality of reagents,
said reagent-dispensing tip (14) is a plurality reagent-dispensing tips, each of which has a configuration adapted to dispense a uniform, prescribed quantity of said reagent that is stored in said container,
wherein each of said container outer surfaces (10a) has indicia (26) that is indicative of one of said characteristic colors which are involved with said screening for one of said medical conditions,
wherein one of said plurality of reagents is a protein reagent that has a configuration adapted to test for the presence of protein when said bodily fluid of said individual is urine, and
wherein said protein reagent includes appropriate quantities of the following components: water, isopropyl alcohol, citric acid monohydrate, sodium citrate tribasic monohydrate, tetrabromophenol blue, and tartrazine.

13. A method of providing a point-of-care screening kit for use by heath care workers to make custom test strips to screen the bodily fluids of an individual for various medical conditions, said method comprising the steps of:
providing a reagent (12),
providing a substrate (18) having an outer surface (18a) that has a configuration adapted to: a) receive said reagent and react with said reagent so as to cause said substrate outer surface to acquire a first characteristic color that is indicative of one of said medical conditions for which said screening is being undertaken, and, b) upon the addition of a specified quantity of said bodily fluid of said individual to a portion of said substrate containing said reagent, acquire a second characteristic color that is indicative of said individual having medical conditions for which said screening is being undertaken,
providing a container (10) having an outer surface (10a) that includes an orifice (10b), said container having a configuration adapted to receive and store a prescribed quantity of said reagent (12), and providing a reagent-dispensing tip (14) that has a configuration adapted to dispense said reagent which is stored in said container.

14. The method of providing the point-of-care screening kit as recited in claim 13, wherein:

said container outer surface (10*a*) has indicia (26) that is indicative of one of said characteristic colors which are involved with said screening for one of said medical conditions.

15. The method of providing the point-of-care screening kit as recited in claim 13, further comprising:

providing a container closing means (16) which has a configuration adapted to cover said reagent-dispensing tip (14) of said container when said reagent-dispensing tip is not in use.

16. The method of providing the point-of-care screening kit as recited in claim 14, further comprising:

providing a container closing means (16) which has a configuration adapted to cover said reagent-dispensing tip (14) of said container when said reagent-dispensing tip is not in use.

17. The method of providing the point-of-care screening kit as recited in claim 15, wherein:

said container closing means (16) has indicia (26) that is indicative of one of said characteristic colors which are involved with said screening for one of said medical conditions.

18. The method of providing the point-of-care screening kit as recited in claim 16, wherein:

said container closing means (16) has indicia (26) that is indicative of one of said characteristic colors which are involved with said screening for one of said medical conditions.

19. The method of providing the point-of-care screening kit as recited in claim 13, wherein:

said reagent (12) has a configuration adapted to yield a dichotomous color change on said substrate, and said substrate is a filter paper having a configuration chosen from the group pre-perforated strips, individual strips and individual sheets.

20. The method of providing the point-of-care screening kit as recited in claim 19, wherein:

said reagent (12) is a protein reagent that has a configuration adapted is configured to test for the presence of protein when said bodily fluid of said individual is urine, and wherein said protein reagent includes appropriate quantities of the following components: water, isopropyl alcohol, citric acid monohydrate, sodium citrate tribasic dihydrate, tetrabromophenol blue and tartrazine.

21. The method of providing the point-of-care screening kit as recited in claim 20, wherein:

said appropriate quantities of said protein reagent components are in the range of: water—5-10 mL, isopropyl alcohol—0-5 mL, citric acid monohydrate—1-1.5 g, sodium citrate tribasic dihydrate—0.22-0.65 g, tetrabromophenol blue—5-15 mg, and tartrazine—0-15 mg.

22. The method of providing the point-of-care screening kit as recited in claim 13, wherein:

said reagent (12) is a plurality of reagents selected from the group consisting of reagents used to screen for: (a) protein, (b) glucose, (c) nitrites, (d) leukocytes, (e) ketone bodies, (f) bilirubin, and (g) urobilinogen, said container (10) is a plurality of containers, each of which has a configuration adapted to receive and store one of said plurality of reagents, said reagent-dispensing tip (14) is a plurality reagent-dispensing tips, each of which has a configuration adapted to dispense a uniform, prescribed quantity of said reagent that is stored in said container with which said reagent-dispensing tip is associated, and wherein each of said container outer surfaces (10*a*) has indicia (26) that is indicative of one of said characteristic colors which are involved with said screening for one of said medical conditions.

23. The method of providing the point-of-care screening kit as recited in claim 22, wherein:

each of said reagents (12) has a configuration adapted to yield a dichotomous color change on said substrate.

24. The method of providing the point-of-care screening kit as recited in claim 13, wherein:

said reagent (12) is a plurality of reagents, each of which has a configuration adapted to yield a dichotomous color change on said substrate, said container (10) is a plurality of containers, each of which has a configuration adapted to receive and store one of said plurality of reagents, said reagent-dispensing tip (14) is a plurality reagent-dispensing tips, each of which has a configuration adapted to dispense a uniform, prescribed quantity of said reagent that is stored in said container, wherein each of said container outer surfaces (10*a*) has indicia (26) that is indicative of one of said characteristic colors which are involved with said screening for one of said medical conditions, wherein one of said plurality of reagents is a protein reagent that has a configuration adapted to test for the presence of protein when said bodily fluid of said individual is urine, and wherein said protein reagent includes appropriate quantities of the following components: water, isopropyl alcohol, citric acid monohydrate, sodium citrate tribasic monohydrate, tetrabromophenol blue, and tartrazine.

\* \* \* \* \*